United States Patent
Uddin et al.

(10) Patent No.: US 9,541,474 B1
(45) Date of Patent: Jan. 10, 2017

(54) SEAWATER SURFACE SAMPLING DEVICE

(71) Applicant: KUWAIT INSTITUTE FOR SCIENTIFIC RESEARCH, Safat (KW)

(72) Inventors: Saif Uddin, Eagila (KW); Montaha Behbahani, Safat (KW)

(73) Assignee: KUWAIT INSTITUTE FOR SCIENTIFIC RESEARCH, Safat (KW)

( * ) Notice: Subject to any disclaimer, the term of this patent is extended or adjusted under 35 U.S.C. 154(b) by 0 days.

(21) Appl. No.: 15/199,850

(22) Filed: Jun. 30, 2016

(51) Int. Cl.
    *G01N 1/14* (2006.01)
    *G01N 33/18* (2006.01)

(52) U.S. Cl.
    CPC ............ *G01N 1/14* (2013.01); *G01N 33/18* (2013.01)

(58) Field of Classification Search
    CPC .................................. G01N 1/14; G01N 33/18
    USPC ........................................................ 73/864.34
    See application file for complete search history.

(56) References Cited

U.S. PATENT DOCUMENTS

| | | | | |
|---|---|---|---|---|
| 4,117,726 | A * | 10/1978 | McGroddy | G01N 1/10 43/6.5 |
| 6,338,282 | B1 * | 1/2002 | Gilbert | G01N 1/14 73/864.34 |
| 2016/0018377 | A1 * | 1/2016 | Corbett | G01N 33/1886 414/137.9 |

FOREIGN PATENT DOCUMENTS

| | | |
|---|---|---|
| CN | 201765131 U | 3/2011 |
| CN | 102862654 A | 1/2013 |
| CN | 204241266 U | 4/2015 |
| JP | 2000-292320 A | 10/2000 |
| KR | 10-0830242 B1 | 5/2008 |
| KR | 10-2014-0073290 A | 6/2014 |

OTHER PUBLICATIONS

Kelley Elliott et al., "NOAA Ship Okeanos Explorer Maximizing Operations: Exploring the 'sticks' in systematic exploration", printed from http://oceanexplorer.noaa.gov/okeanos/explorations/ex1006/welcome.html; 4 pages, printed on May 17, 2016.

* cited by examiner

*Primary Examiner* — Hezron E Williams
*Assistant Examiner* — David Z Huang
(74) *Attorney, Agent, or Firm* — Richard C. Litman

(57) ABSTRACT

The seawater surface sampling device is a buoyant device for sampling the topmost layer of water in a body of water in order to study water properties specific to depths of only about 0.5 cm. The seawater sampling device includes a buoyant housing having an open upper end, a lower wall and at least one sidewall. The lower wall has a concave contour, and an aperture is formed through the lower wall at an apex of the concave contour. A pump is mounted on an upper surface of the lower wall, within the buoyant housing, and is in fluid communication with the aperture for extracting the water sample therethrough. A sample holder is also mounted on the upper surface of the lower wall, within the buoyant housing, for removably receiving a sample collection bottle.

10 Claims, 3 Drawing Sheets

SEAWATER SURFACE SAMPLING DEVICE

BACKGROUND OF THE INVENTION

1. Field of the Invention

The present invention relates to measurement and testing of seawater and the like, and particularly to a seawater surface sampling device that samples water only in the topmost layer of a body of water.

2. Description of the Related Art

There exists a great deal of variety in the contents of seawater (and water contained in other natural bodies of water) based on depth from the water's surface. The topmost 0.5 cm of seawater is of particular interest, as it is highly concentrated with phytoplankton and zooplankton. Additionally, a wide variety of surface-atmospheric interactions, taxonomic diversity, the partial pressure of carbon dioxide, and contaminants (such as radionucleides) are of interest in numerous fields of study. Although a wide variety of techniques for sampling water exist, ranging from simple bottles which are dipped into the water to robotic skimmers, such devices typically collect the water from mixed depths including far more than just the topmost 0.5 cm surface layer. It would be desirable to be able to easily sample water taken just at the topmost surface layer. Thus, a seawater surface sampling device solving the aforementioned problems is desired.

SUMMARY OF THE INVENTION

The seawater surface sampling device is a buoyant device for sampling the topmost layer of water in a body of water in order to study water properties specific to depths of only about 0.5 cm, such as surface-atmospheric interactions, phytoplankton concentrations, partial pressure of carbon dioxide, radionuclides and the like. The seawater sampling device includes a buoyant housing having an open upper end, a lower wall and at least one sidewall. The lower wall has opposed upper and lower surfaces, with the lower surface having a concave contour. An apex of the concave contour is vertically positioned higher than a pair of side edges of the lower surface. An aperture is formed through the lower wall at the apex.

A pair of stabilizing members are preferably secured to the buoyant housing. The stabilizing members are preferably also buoyant such that, when placed in the body of water, a lower surface of each stabilizing member rests on the water's surface. In order to sample the water in the desired depth near the surface, a vertical distance between the lower surface of each stabilizing member and the apex of the lower wall is between approximately 1 mm and approximately 2 mm.

A pump is mounted on the upper surface of the lower wall, within the buoyant housing, and is in fluid communication with the aperture for extracting the water sample through the aperture. A sample holder is also mounted on the upper surface of the lower wall, within the buoyant housing, and is adapted for removably receiving a sample collection bottle. In use, when the buoyant housing floats on the surface of the body of water, the pump extracts the water sample through the aperture formed through the lower wall of the buoyant housing and outputs the water sample to the sample collection bottle through an output tube connected to the pump.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
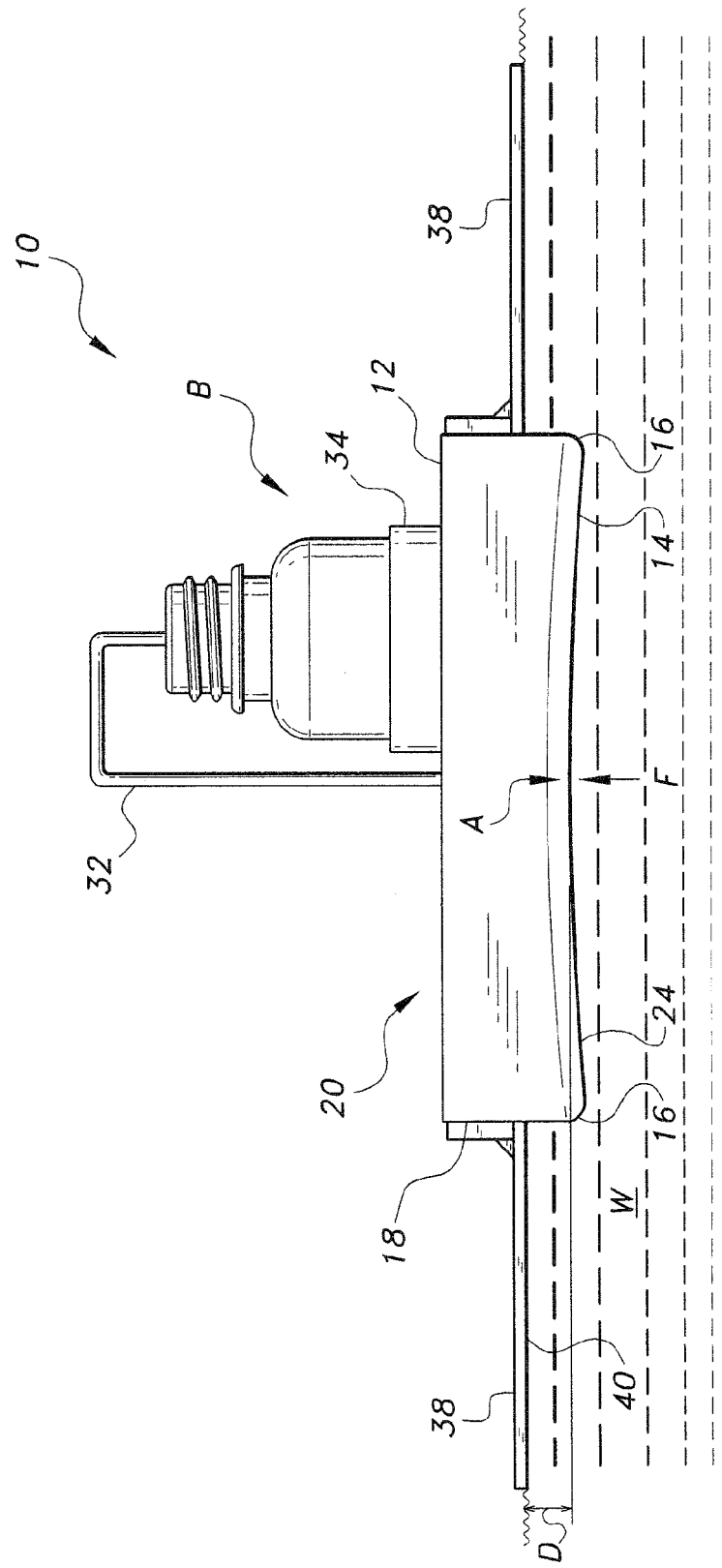
FIG. 1 is an environmental side view of a seawater surface sampling device according to the present invention.
Figure 2:
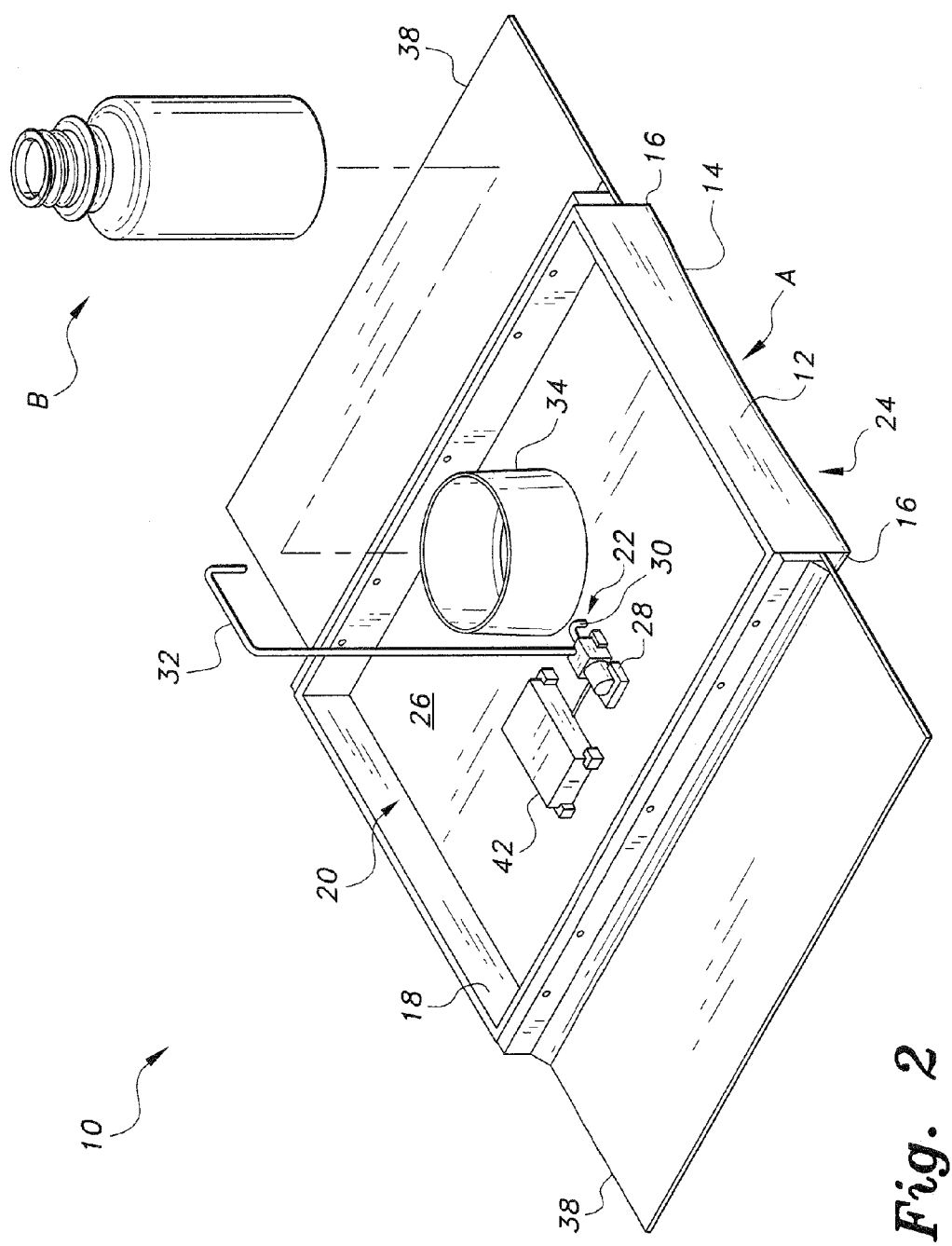
FIG. 2 is a top perspective view of the seawater surface sampling device according to the present invention.

Referring now to FIG. 1, the seawater surface sampling device 10 is a buoyant device for sampling the topmost layer of water in a body of water W, for example the top 0.5 cm of seawater, to study surface-atmospheric interactions, phytoplankton concentrations, partial pressure of carbon dioxide, radionucleides and the like. As shown in FIGS. 1 and 2, the seawater sampling device 10 includes a buoyant housing 12 having an open upper end 20, a lower wall 14 and at least one sidewall 18. Although shown as having a substantially rectangular cross-sectional contour in FIGS. 1 and 2, it should be understood that buoyant housing 12 may have any desired overall contouring and relative dimensions.

Figure 3:
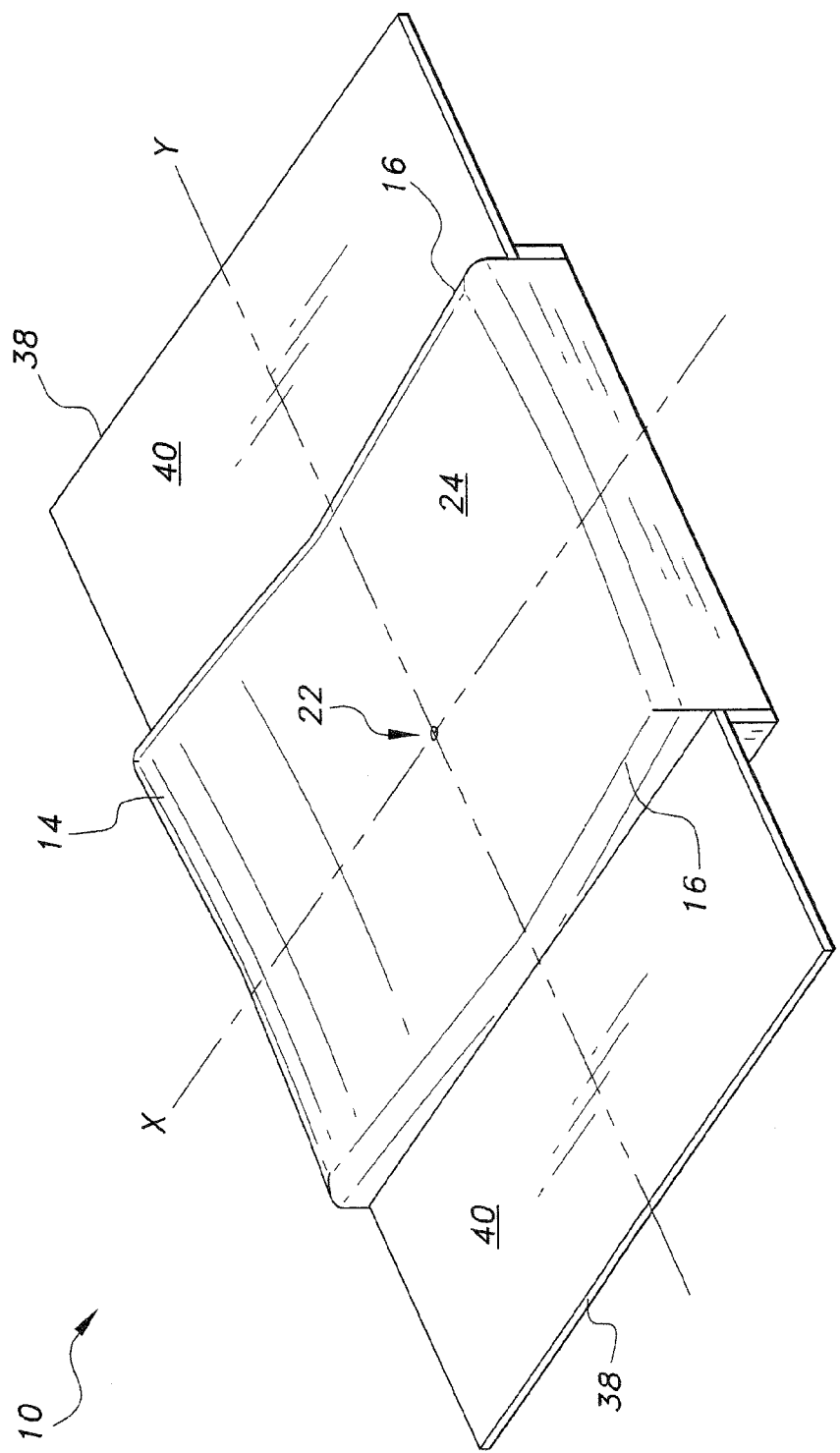
FIG. 3 is a bottom perspective view of the seawater surface sampling device according to the present invention.

The lower wall 14 has opposed lower and upper surfaces, 24, 26, respectively, with the lower surface 24 having a concave contour. As best seen in FIG. 1, an apex A of the concave contour is vertically positioned higher than a pair of side edges 16 of the lower surface 24 of lower wall 14. As best shown in FIG. 3, the concave contouring of lower surface 24 is preferably three-dimensional; i.e., the lower surface 24 has an arcuate cross-sectional contour along both the x-axis and the y-axis (shown in FIG. 3 as orthogonal lateral and longitudinal axes, respectively). An aperture 22 is formed through the lower wall 14 at the apex A of the curvature.

A pair of stabilizing members 38 are preferably secured to the buoyant housing 12. The stabilizing members 38 are preferably also buoyant such that, when placed in the body of water, a lower surface 40 of each stabilizing member 38 rests on the water's surface, as shown in FIG. 1. Although stabilizing members 38 are shown as rectangular plates, similar to conventional stabilizing wings or the like, it should be understood that stabilizing members 38 may have any desired overall contouring or relative dimensions. The lower surface 40 of each stabilizing member 38 can be in line with the apex A of the lower wall 14. Alternatively, a vertical distance D between the lower surface 40 of each stabilizing member 38 and the apex A of the lower wall 14 (or, alternatively, the vertical distance between the water surface and apex A) can be between approximately 1 mm and approximately 2 mm.

As shown in FIG. 1, a pump 28 is mounted on the upper surface 26 of the lower wall 14, within the buoyant housing 12, and is in fluid communication, via tube 30, with the aperture 22 for extracting the water sample through aperture 22. It should be understood that any suitable type of pump, such as a conventional 3 V micropump, for example, may be utilized. A suitable source of power, such as a conventional battery 42 or the like, may also be mounted on upper surface 26 of lower wall 14 for powering the pump 28.

A sample holder 34 is also mounted on the upper surface 26 of lower wall 14, within the buoyant housing 12, and is adapted for removably receiving a sample collection bottle B. It should be understood that sample collection bottle B is shown for exemplary purposes only, and that the overall contouring and relative dimensions of sample holder 34 may be varied dependent upon the size and type of bottle B used.

In use, when the buoyant housing 12 floats on the surface of the body of water W, the pump 28 extracts the water sample through the aperture 22 formed through the lower wall 14 of buoyant housing 12 (indicated by water flow F in FIG. 1). The water sample is output, via an output tube 32, to the sample collection bottle B held within sample holder 34. The pump 28 preferably operates at a low elution rate, preferably of approximately 8 mL/min to approximately 10 mL/min, and this low elution rate, combined with the concave lower surface 24 of lower wall 14, ensures that only water from approximately 1 mm to approximately 2 mm below the surface is sampled.

It is to be understood that the present invention is not limited to the embodiments described above, but encompasses any and all embodiments within the scope of the following claims.

We claim:

1. A seawater surface sampling device, comprising:
   a buoyant housing having an open upper end, a lower wall and at least one sidewall, the lower wall having opposed upper and lower surfaces, the lower surface thereof having a concave contour such that an apex thereof is vertically positioned higher than a pair of side edges of the lower surface, an aperture being formed through the lower wall at the apex;
   a pump in fluid communication with the aperture;
   an output tube in fluid communication with the pump; and
   a sample holder adapted for removably receiving a sample collection bottle, whereby when said buoyant housing floats on a surface of a body of water, the pump extracts a water sample through the aperture formed through the lower wall of the buoyant housing and outputs the water sample to the sample collection bottle through the output tube.

2. The seawater surface sampling device as recited in claim 1, further comprising a pair of stabilizing members secured to the buoyant housing.

3. The seawater surface sampling device as recited in claim 2, wherein a vertical distance between a lower surface of each said stabilizing member and the apex is approximately 1 mm to approximately 2 mm.

4. The seawater surface sampling device as recited in claim 2, wherein a lower surface of each stabilizing member is in line with the apex of the lower wall.

5. The seawater surface sampling device as recited in claim 1, wherein said pump is mounted on the upper surface of the lower wall of the buoyant housing.

6. The seawater surface sampling device as recited in claim 5, wherein said sample holder is mounted on the upper surface of the lower wall of the buoyant housing.

7. A seawater surface sampling device, comprising:
   a buoyant housing having an open upper end, a lower wall and at least one sidewall, the lower wall having opposed upper and lower surfaces, the lower surface thereof having a concave contour such that an apex thereof is vertically positioned higher than a pair of side edges of the lower surface, an aperture being formed through the lower wall at the apex;
   a pair of stabilizing members secured to the buoyant housing;
   a pump in fluid communication with the aperture;
   an output tube in fluid communication with the pump; and
   a sample holder adapted for removably receiving a sample collection bottle, whereby when said buoyant housing floats on a surface of a body of water, the pump extracts a water sample through the aperture formed through the lower wall of the buoyant housing and outputs the water sample to the sample collection bottle through the output tube.

8. The seawater surface sampling device as recited in claim 7, wherein said pump extracts the water sample at a rate of between approximately 8 mL/min and approximately 10 mL/min.

9. The seawater surface sampling device as recited in claim 7, wherein said pump is mounted on the upper surface of the lower wall of the buoyant housing.

10. The seawater surface sampling device as recited in claim 9, wherein said sample holder is mounted on the upper surface of the lower wall of the buoyant housing.

* * * * *